United States Patent
Kwon et al.

(10) Patent No.: US 9,920,667 B2
(45) Date of Patent: Mar. 20, 2018

(54) WATER DRAIN SYSTEM FOR OIL RESERVE TANK

(71) Applicants: SK Innovation Co., Ltd., Seoul (KR); SK Energy Co., Ltd., Seoul (KR)

(72) Inventors: Chi Myong Kwon, Ulsan (KR); Jang Heon Lee, Ulsan (KR); Hee Duck Park, Ulsan (KR); Hye Min Choi, Ulsan (KR); Yoo Keun Kim, Ulsan (KR); Ki Young Bae, Ulsan (KR); Cheol Hong, Ulsan (KR)

(73) Assignees: SK Innovation Co., Ltd., Seoul (KR); SK Energy Co., Ltd., Seoul (KR)

( * ) Notice: Subject to any disclaimer, the term of this patent is extended or adjusted under 35 U.S.C. 154(b) by 189 days.

(21) Appl. No.: 14/409,677

(22) PCT Filed: Jun. 19, 2013

(86) PCT No.: PCT/KR2013/005410
§ 371 (c)(1),
(2) Date: Dec. 19, 2014

(87) PCT Pub. No.: WO2013/191467
PCT Pub. Date: Dec. 27, 2013

(65) Prior Publication Data
US 2015/0152759 A1    Jun. 4, 2015

(30) Foreign Application Priority Data
Jun. 22, 2012 (KR) .......................... 10-2012-0067460

(51) Int. Cl.
*F01M 11/03* (2006.01)
*F01M 11/10* (2006.01)
(Continued)

(52) U.S. Cl.
CPC ............ *F01M 11/03* (2013.01); *C10G 33/06* (2013.01); *F01M 11/10* (2013.01);
(Continued)

(58) Field of Classification Search
CPC ........ C10G 33/06; C10G 33/08; F01M 11/03; F01M 11/10; C02F 1/40; C02F 2101/32;
(Continued)

(56) References Cited

U.S. PATENT DOCUMENTS

| | | | |
|---|---|---|---|
| 3,216,915 A * | 11/1965 | Arthur | G01N 27/38 204/402 |
| 9,086,354 B2 * | 7/2015 | AlSahan | B01D 17/0214 |
| 2014/0130251 A1 * | 5/2014 | Yu | E03C 1/29 4/679 |

FOREIGN PATENT DOCUMENTS

| | | |
|---|---|---|
| CN | 2209762 Y | 10/1995 |
| CN | 2825641 Y | 10/2006 |

(Continued)

OTHER PUBLICATIONS

English Machine Translation of JP10-137506A, May 1998.*
(Continued)

*Primary Examiner* — Terry K Cecil
(74) *Attorney, Agent, or Firm* — Abelman, Frayne & Schwab

(57) ABSTRACT

The present invention relates to a water drain system of an oil reserve tank, which comprises: an oil reserve tank; an oil and water separator for separating the drained water coming from the oil reserve tank; a drain pipe extended from the oil reserve tank to the oil and water separator, the drain pipe having a vertical part to form a step; and a water detection sensor installed in the vertical part.

7 Claims, 4 Drawing Sheets

(51) Int. Cl.
  *G01N 27/38* (2006.01)
  *C10G 33/06* (2006.01)
  *F16N 39/00* (2006.01)
  *F16N 39/06* (2006.01)
  *B01D 17/02* (2006.01)
  *C10G 33/08* (2006.01)
  *G01F 23/00* (2006.01)
  *C02F 1/40* (2006.01)
  *C02F 101/32* (2006.01)

(52) U.S. Cl.
  CPC .......... *F16N 39/005* (2013.01); *F16N 39/06* (2013.01); *G01N 27/38* (2013.01); *B01D 17/0214* (2013.01); *C02F 1/40* (2013.01); *C02F 2101/32* (2013.01); *C10G 33/08* (2013.01); *F01M 2011/146* (2013.01); *G01F 23/0007* (2013.01)

(58) Field of Classification Search
  CPC .............. B01D 17/0214; B01D 17/025; B01D 17/032; B01D 17/12; G01N 27/38
  See application file for complete search history.

(56) References Cited

FOREIGN PATENT DOCUMENTS

| | | |
|---|---|---|
| CN | 201191282 Y | 2/2009 |
| JP | 10137506 A * | 5/1998 |
| JP | 2003034400 A | 2/2003 |
| JP | 4031542 B2 | 1/2008 |
| KR | 100181540 B1 | 3/1999 |
| KR | 1020010036118 A | 5/2001 |
| KR | 1020020027752 A | 4/2002 |

OTHER PUBLICATIONS

PCT Publication with International Search Report for priority PCT/KR2013/005410; dated Dec. 27, 2013; 16 pages.

Search Report and Written Opinion in counterpart Chinese Application No. 201380038859.5; dated Nov. 18, 2016; 9 pages.

* cited by examiner

SLUDGE REMOVAL STAGE

CLEANING UNIT REPLACEMENT STAGE

WATER DRAIN SYSTEM FOR OIL RESERVE TANK

CLAIM FOR PRIORITY

This application claims priority to PCT/KR2013/005410, filed 19 Jun. 2013, which claims benefit to Korean Patent Application No. 10-2012-0067460, filed on 22 Jun. 2012.

TECHNICAL FIELD

The present invention relates to a water drain system for an oil reserve tank that drains water from the oil reserve tank.

BACKGROUND ART

Oil reserve tanks store oil used for various types of engines, industries, etc. When water or particulate contaminants are mixed in oil, the impure oil is likely to cause malfunctioning of machines.

Moreover, when oil containing water is supplied to an engine, the water in the oil corrodes parts of the engine, causing fatal damage to the engine, leading to start failure or abrupt stopping of the engine.

To this end, a conventional water removal system for removing water from oil is disclosed in Patent Document 1. Patent Document 1 is Japanese Patent Application Publication No. 2003-34400 titled "Drain Detector for Oil Reserve Tank".

The drain detector disclosed in Patent Document 1 includes a level sensor that is installed on the bottom of an oil reserve tank and a display unit that is electrically connected to the level sensor. The display unit is installed outside the oil reserve tank.

According to the conventional drain detector, when drain water gravitates toward the bottom of the oil reserve tank and reaches a level at which the level sensor is mounted, the level sensor detects the level of the drain water and sends a signal to the display unit. In this way, the drain detector issues a warning.

When an operator recognizes this warning, the operator opens a valve on a drain pipe to discharge the drain water outside the oil reserve tank.

The drain detector disclosed in Patent Document 1 features the arrangement in which the level sensor is mounted on the inside bottom of the oil reserve tank. However, since the level sensor is not fixed in place on the bottom of the oil reserve tank, sometimes the level sensor cannot accurately detect the level of the drain water. In this case, the level of the drain water cannot be reliably measured.

In addition, since the level sensor is submerged in oil in which water or contaminants are mixed, the level sensor is highly likely to be contaminated. The contaminated level sensor cannot be replaced or cleaned until the oil is completely discharged outside the oil reserve tank.

For this reason, there is the demand for solving this problem.

RELATED ART DOCUMENT

Patent Document

Patent Document 1: Japanese Patent Application Publication No. 2003-34400

DISCLOSURE

Technical Problem

Accordingly, the present invention has been made keeping in mind the above problems occurring in the related art, and an object of the present invention is to continuously and promptly detect water mixed in oil using a water detection sensor that is installed to extend from a bottom portion of an oil reserve tank to an inside of a drain pipe.

Technical Solution

In order to accomplish the above objects, according to one aspect, there is provided a water drain system for an oil reserve tank, including: an oil reserve tank; an oil-water separator separating drain water supplied from the reserve tank into oil and water; a drain pipe horizontally extending from the oil reserve tank to the oil-water separator and taking a step form by having a vertical portion; and a water sensor installed in the vertical portion of the drain pipe.

The drain pipe may be step-shaped to enable an upward stream of the drain water that is composed of water and oil and is discharged from the bottom of the oil reserve tank.

The water drain system may further include a cleaning unit that removes sludge adhered to the water detection sensor and that is arranged in a position that faces the water sensor in a radial direction of the drain pipe.

The water drain system may further include a first valve that controls drainage of the drain water through the drain pipe that extends from a lower portion of the oil reserve tank.

The water drain system may further include a third valve that is installed in the cleaning unit and near a position at which the drain pipe and the cleaning unit intersect each other.

The water drain system may further include a return pipe through which oil separated from the drain water by the oil-water separator is returned to the oil reserve tank.

The water drain system may further include a sump that is located downstream from the oil-water separator, thereby discharging water and contaminants separated from the drain water to a wastewater treatment plant.

The cleaning unit may optionally include a brush that moves to approach and retreat from the water detection sensor installed in the drain pipe, thereby wiping out and removing sludge adhered to the water detection sensor.

The above and other objects, features and other advantages of the present invention will be more clearly understood from the following detailed description when taken in conjunction with the accompanying drawings.

All terms used in this disclosure and claims should not be interpreted as having the same meaning as commonly understood or defined in common dictionaries, but be interpreted as having a meaning that is consistent with their meaning in the context of the relevant art, based on the principle that applicants are their own lexicographers and can define what they regard as their invention essentially in whatever terms they choose.

Advantageous Effects

According to the present invention, it is possible to detect the water content in oil while drain water is being drained from the oil reserve tank.

According to the invention, since it is possible to remove sludge on the water detection sensor even while drain water is flowing, it is possible to maximize water-oil separation efficiency while reducing labor time.

According to the invention, the cleaning unit that removes sludge on the water detection sensor is included. In addition, the cleaning unit is structured in such a manner that the brush thereof can be replaced or repaired or both even while drain water is flowing.

The water drain system according to the present invention can improve the sensing efficiency of the water detection sensor by causing the drain water that flows through the drain pipe to flow upward and by causing the drain water to flow in the state in which the drain pipe is filled with the drain water.

BEST MODE

Figure 1:
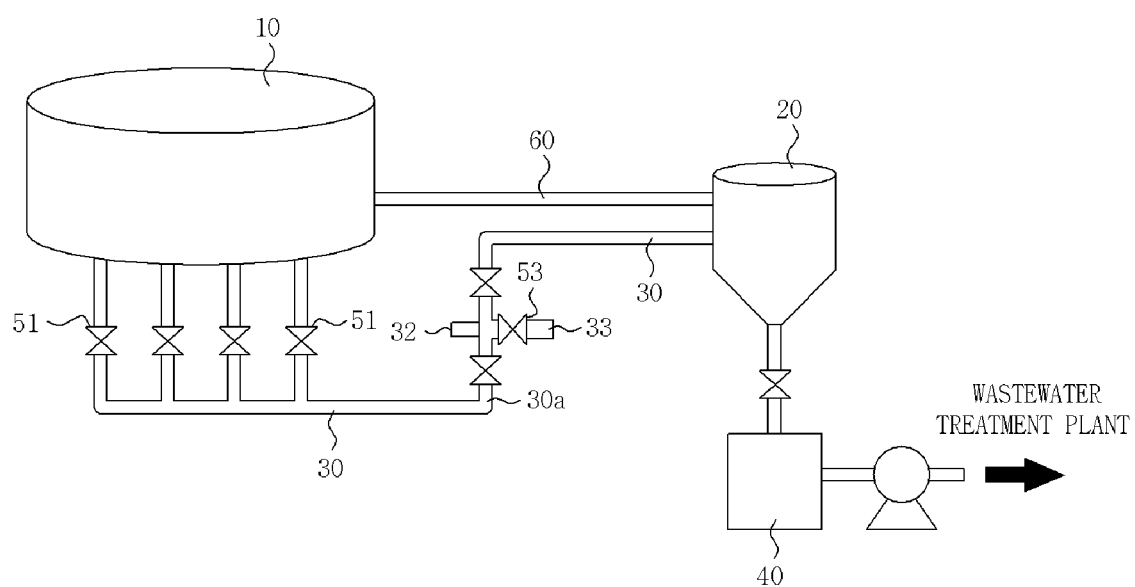
FIG. 1 is a diagram that schematically illustrates a water drain system for an oil reserve tank according to one embodiment.

Hereinafter, a water drain system for an oil reserve tank will be described in detail with reference to the accompanying drawings.

The above and other objects, features and other advantages of the present invention will be more clearly understood from the following detailed description when taken in conjunction with the accompanying drawings. As for reference numerals associated with parts in the drawings, the same reference numerals will refer to the same or like parts through the drawings. In the description, details of well-known features and techniques may be omitted to avoid unnecessarily obscuring the presented embodiments.

FIG. 1 is a diagram that schematically illustrates a water drain system for an oil reserve tank according to the present invention.

As illustrated in the drawing, the water drain system for an oil reserve tank includes an oil reserve tank 10, an oil-water separator 20, a drain pipe 30, and a sump 40. The water drain system according to the present invention can measure the water content in oil in real time when drain water is being drained from the oil reserve tank 10.

As described above, the water drain system according to the present invention is designed to discharge drain water that is produced from oil-water mixtures in the oil reserve tank 10, periodically in automatic mode or occasionally by an operator.

The oil reserve tank 10 is a chamber for storing oil. The oil-water separator 20 separates the drain water into water and oil and separately collects the water and oil. The oil reserve tank 10 and the oil-water separator 20 are well-known technologies that are known to people skilled in the art. Accordingly, a description about these technologies will be omitted to aid clear understanding of the present invention.

The drain water contains water or contaminants or both as well as oil as described above. The drain water is guided to the oil-water separator 20 after being drained from the oil reserve tank 10 and then separated into oil and water-contaminant mixtures. The water or contaminants or both that are separated from the drain water are guided to the sump 40. Then, the water or contaminants or both stored in the sump 40 are discharged to a wastewater treatment plant.

Optionally, the oil-water separator 20 has a water detection sensor (not shown) therein, thereby measuring the water content in oil supplied to the oil-water separator 20. When the water content is a predetermined value or less, the oil is returned to the oil reserve tank 10 through a return pipe 60. On the other hand, when the water content is the predetermined value or more, the oil is discharged to the sump 40 and the wastewater treatment plant.

The drain water in the oil reserve tank 10 may be guided to the oil-water separator 20 through a drain pipe 30 that extends from the oil reserve tank 10 to the oil-water separator 20.

The drain pipe 30 is provided with a first valve 51, a water detection sensor 32, and a cleaning unit 33. The cleaning unit 33 removes sludge that settles on the water detection sensor 32 by coming into contact with the water-containing oil.

The drain pipe 30 is an elongated pipe. Preferably, a portion of the drain pipe 30 vertically extends with respect to the ground surface.

The water detection sensor 32 is installed in the vertical portion 30a of the drain pipe 30. The water detection sensor 32 measures the water content in oil that contains water, called drain water, which is drained from the oil reserve tank 10. Since the water detection sensor 32 is installed in the vertical portion 30a of the drain pipe 30, sufficient contact between the oil and the water detection sensor 32 is secured while precipitation of sludge to the water detection sensor 32 is prevented. The water detection sensor 32 measures the water content in the drain water that passes through the vertical portion 30a of the drain pipe 30. When the water content in the drain water is a predetermined value or more, the on-going operation is continued. However, when the water content in the drain water is the predetermined value or less, the first valve 51 is closed so that the oil that contains less water than the predetermined amount cannot be discharged through the drain pipe 30.

Specifically, since the water detection sensor 32 is installed in the vertical portion 30a of the drain pipe in which the drain water flows upward, a period of time during which the water detection sensor 32 is in contact with the oil is minimized, preventing precipitation of sludge to the water detection sensor 32 and improving measurement reliability of the water content.

The vertical portion 30a of the drain pipe enables an upward stream of the drain water drained from the oil reserve tank 10. In other worlds, the vertical portion 30a of the drain pipe enables the drain water to flow upward. The drain water flows upward in a state in which the drain water fills up the inside of the vertical portion 30a of the drain pipe 30.

The operation performance of the water detection sensor 32 is deteriorated due to the sludge that settles on the water detection sensor 32 over time. The cleaning unit 33 is installed to remove sludge that settles on the water detection sensor 21. The cleaning unit 33 is preferably associated with the vertical portion 30a of the drain pipe 30, and more specifically is located to face the water detection sensor 32 associated with the vertical portion 30a of the drain pipe 30.

Figure 2:
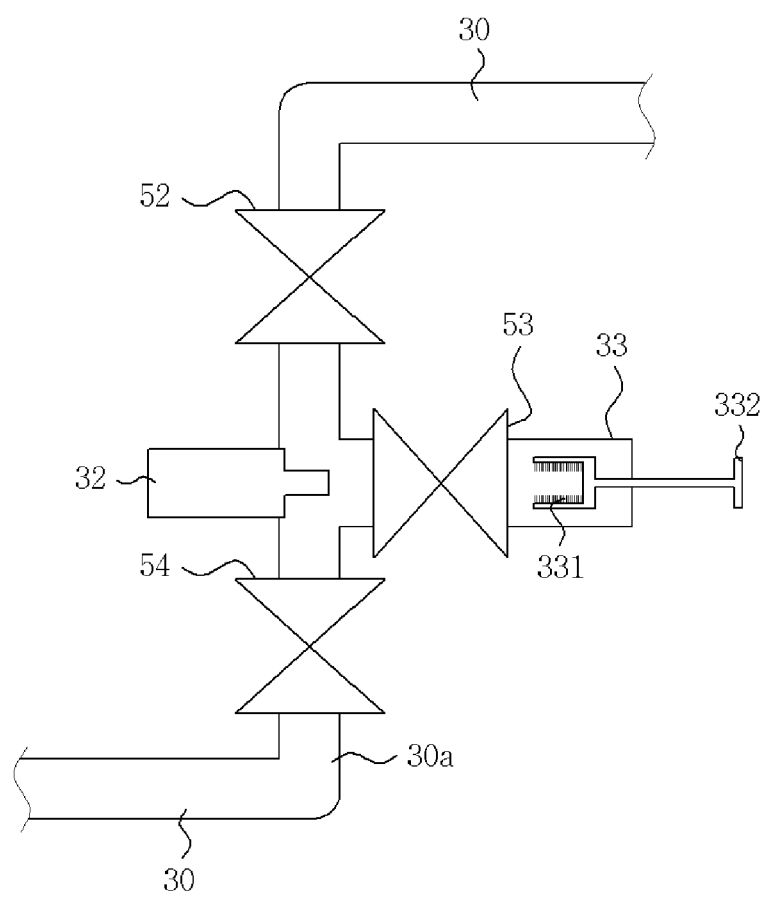
FIG. 2 is a cross-sectional view that schematically illustrates a drain pipe of the water drain system according to the embodiment.

FIG. 2 schematically illustrates a portion of the drain pipe of the water drain system according to the present invention. FIG. 2 is a cross-sectional view that shows a portion of the vertical portion of the drain pipe and that shows arrangement of the water detection sensor 32 and the cleaning unit 33.

An end of the water detection sensor 32 is inserted into and fixed to the vertical portion 30a of the drain pipe so that it is arranged to come into contact with the drain water that flows upward in the vertical portion 30a of the drain pipe 30.

The cleaning unit 33 has an elongated tube form that extends in parallel with the ground surface or in perpendicular to the lengthwise direction of the vertical portion 30a of the drain pipe 30. The cleaning unit 33 includes a hollow brush 331 and a bar 332. The bar 332 extends to pass through an end, in the lengthwise direction, of the tube-shaped cleaning unit 33 and is connected to the brush 331.

The slidable brush 331 is moved back and forth, toward and from the inside of the vertical portion 30a of the drain pipe or is rotated by driving force of the bar 332 or both. The water detection sensor 32 is cleaned by reciprocating movement of the hollow brush. The brush 331 retreats into and stays inside the cleaning unit 33 except for a period during which the brush 331 removes sludge so as to secure the smooth flow of the drain water.

The cleaning unit 33 is arranged in the opposite side of the water detection sensor 32 with respect to the vertical portion 30a of the drain pipe 30 so that the brush 331 and the water detection sensor 32 can be easily aligned.

The sludge that is removed from the surface of the water detection sensor by the operation of the cleaning unit 33 is sent to the oil-water separator along with the stream of the drain water that flows through the drain pipe 30.

As illustrated in the drawing, the cleaning unit 33 includes a third valve 53 that is installed in a position at which the vertical portion of the drain pipe 30 and the cleaning unit face each other. The third valve 53 is closed when the brush 331 is replaced. When the valve 53 is closed, the drain water that flows through the drain pipe 30 is not introduced into the cleaning unit 33. Accordingly, the cleaning unit 33 can be detached from the drain pipe 30 so that the brush 331 can be replaced or repaired. Regardless of the replacement work of the brush, the drain water is allowed to continuously flow downward.

The vertical portion 30a of the drain pipe 30 is a portion of the drain pipe 30 which extends from the oil reserve tank 10 to the oil-water separator 20 in a manner of communicating with the oil reserve tank 10 and the oil-water separator 20. The drain pipe 30 takes a step form by having the vertical portion 30a. The drain pipe 30 illustrated in the drawing takes a step form by having the vertical portion that is a straight pipe, but the drain pipe 30 is not limited to this form. That is, the drain pipe 30 may be a U-shaped pipe or a reversed-U-shaped pipe or may be arranged to be inclined at a predetermined angle with respect to the ground surface.

The drain pipe 30 that provides a stream path such as the vertical portion 30a allows the drain water to flow upward in a state in which the drain pipe is filled with the drain water. Therefore, the drain water that flows through the vertical portion 30a can come into contact with almost the entire surface of the water detection sensor 32 installed in the vertical portion 30a. When the drainage of the drain water is blocked, the drain water cannot come into contact with the water detection sensor 32 because of the specially designed structure of the vertical portion 30a. Accordingly, it is possible to prevent sludge contained in the drain water from settling on the water detection sensor 32.

The water drain system according to the present invention further includes a fourth valve 54 and a second valve 52 that are installed on the path of the drain pipe 30. Preferably, the fourth valve 54 is arranged upstream from the water detection sensor 32 and the second valve 52 is arranged downstream from the water detection sensor 32.

In the water drain system according to the present invention, when the first valve 51 (shown in FIG. 1) and the second valve 52 are closed and the inside of the drain pipe 30 is evacuated, the water detection sensor 32 can be replaced or repaired or both.

In addition, when repairing the water detection sensor 32 or the cleaning unit 33 or both, the fourth valve 54 and the second valve 52 may be closed. That is, since a small amount of the drain water remains in a portion of the drain pipe 30 that is arranged upstream from the water detection sensor 32, the fourth valve 54 is closed so that the remaining drain water cannot be drained outside. Similarly, the second valve 52 is closed so that the remaining drain water in a portion of the drain pipe 30 that is arranged downstream from the water detection sensor 32 cannot be discharged outside by the backflow of the drain water.

FIGS. 3a to 3d are schematic diagrams illustrating operation states of the drain pipe of the water drain system according to the present invention. Here, to aid understanding about the measurement of the water content in oil while securing the contact between the water detection sensor and the oil that contains water, which is discharged from the oil reserve tank 10, the states of the drain pipe of the water drain system according to the present invention are differentiated in the illustration. In order to differentiate the states of the stream of the drain water that is guided through the drain pipe 30 (or 30a), the drain pipe in which there is the stream of the drain water is colored black, and the drain pipe in which there is no stream of drain water is not colored. On the other hand, in order to explicitly show the filling state of oil or drain water in the oil reserve tank 10, the inside of the oil reserve tank 10 is not colored.

Figure 3A:
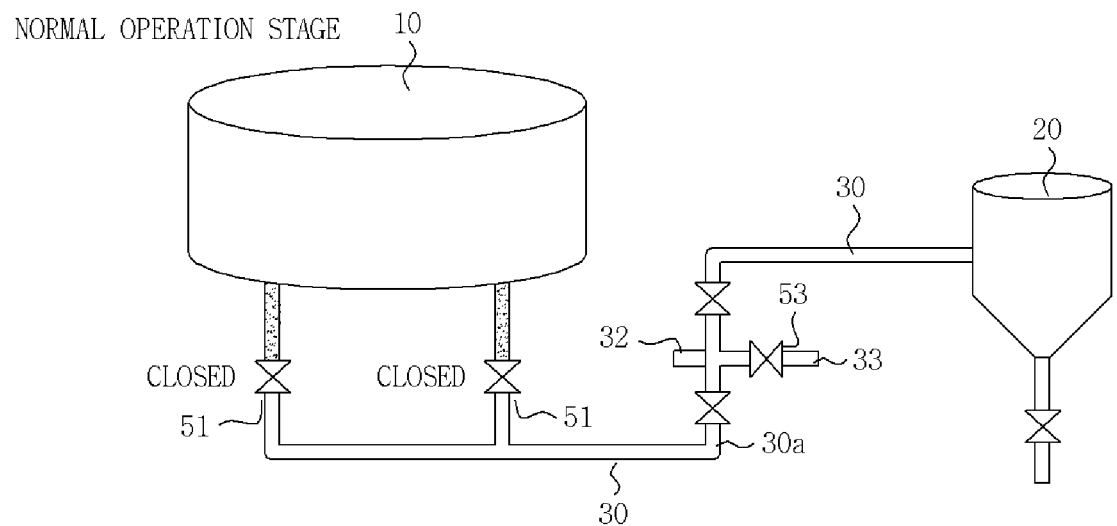
FIGS. 3a to 3d are diagrams that illustrate operation states of the drain pipe of the water drain system according to the embodiment.

FIG. 3a is a diagram illustrating a normal operation stage of the oil reserve tank 10.

In this normal operation stage, the water content in oil stored in the oil reserve tank 10 is low. Thus, water removal is not performed. The oil is stored in the oil reserve tank 10 or transported outside through an oil transportation pipe (not shown) as necessary. Therefore, the first valve 51 is closed so that oil cannot flow downstream through the drain pipe 30.

Figure 3B:
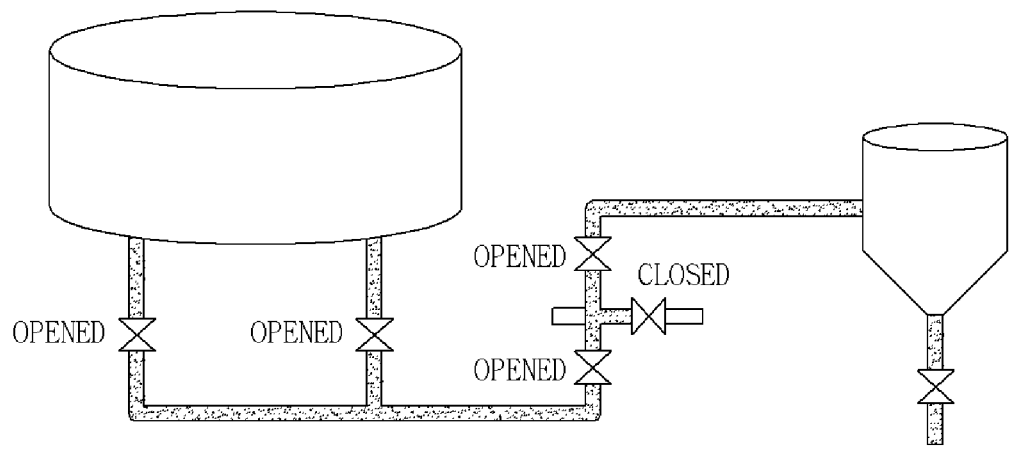

FIG. 3b is a diagram illustrating a drain water drainage stage in which drain water is discharged outside the oil reserve tank 10.

At the time draining drain water, the first valve 51, the fourth valve 54 (shown in FIG. 2), and the second valve 52 (shown in FIG. 2) provided on the drain pipe 30 are opened. Thus, the drain water that collects on the bottom of the oil reserve tank 10 passes around the water detection sensor 32 and reaches the oil-water separator 20, and then the drain water is separated into oil and water by the oil-water separator 20. In the vertical portion 30a of the drain pipe, the water detection sensor 32 measures the water content in the drain water. When the water content in the drain water is a predetermined value or more, the first valve 51 is continuously open and the drain water continuously flows downstream to the oil-water separator 20. Thus, the drain water is continuously separated into oil and water by the oil-water separator 10. The separated water is drained to the wastewater treatment plant through the sump 40 (shown in FIG. 1), and the separated oil may be returned to the oil reserve tank 10 through the return pipe 60 (shown in FIG. 1).

As illustrated in the drawings, the water detection sensor 32 is installed in the vertical portion 30a of the drain pipe to generate the upward stream of the drain water. The drain water flows upward in the state in which the vertical portion 30a of the drain pipe is filled with the drain water.

Figure 3C:
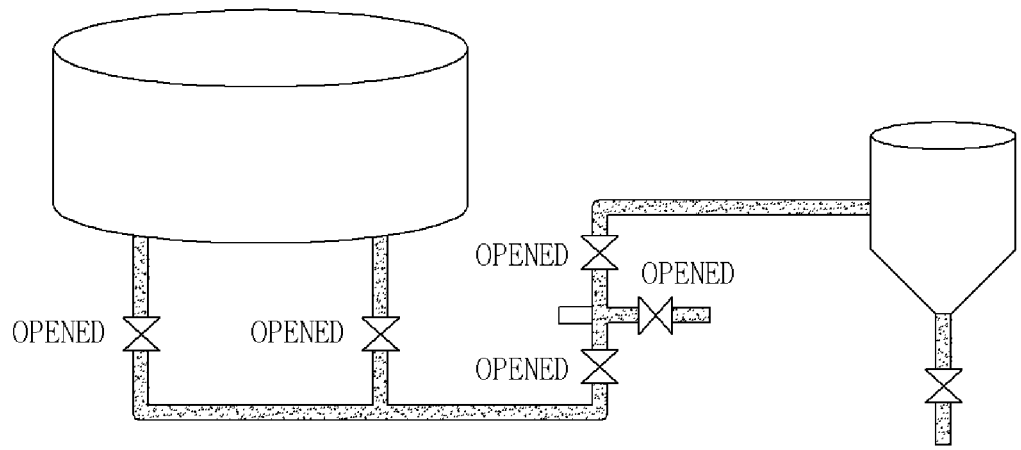

FIG. 3c is a diagram illustrating a sludge removal stage at which sludge is removed from the oil reserve tank 10.

When drain water is drained for a long period of time, the water detection sensor 32 is surrounded by sludge due to water or contaminants or both contained in the drain water. In this case, due to the sludge (not shown), the water detection sensor 32 cannot effectively come into contact with the drain water that flows through the drain pipe. Thus, the water detection sensor 32 cannot accurately detect the water content in the drain water. For this reason, the first valve 51 is opened unnecessarily, so the low-water-content oil may be discharged. Conversely, the first valve 51 is erroneously closed so that the drain water in the oil reserve tank 10 cannot be drained outside.

In order to solve this problem, at the time of removing sludge, the third valve 53 is opened and the first vale 51 is also opened. The brush 331 (shown in FIG. 2) of the cleaning unit 33 is driven to move forward to be inserted into the vertical portion 30a of the drain pipe. The brush comes into contact with the water detection sensor 32, removing the sludge adhered to the water detection sensor 32. The drain water can continuously flow through the drain pipe 30.

While the brush that is moved into the vertical portion of the drain pipe is removing the sludge, since the water detection sensor 32 is in contact with the brush, the water detection sensor 32 may come into non-uniform contact with the drain water that flows through the drain pipe 30. Thus, the water detection sensor 32 cannot accurately measure the water content in the drain water. The vertical portion of the drain pipe may be provided with an auxiliary water detection sensor (not shown). The auxiliary water detection sensor is at a predetermined distance from the water detection sensor 32 to avoid collision with the brush while the brush moves forward or backward or both.

Figure 3D:
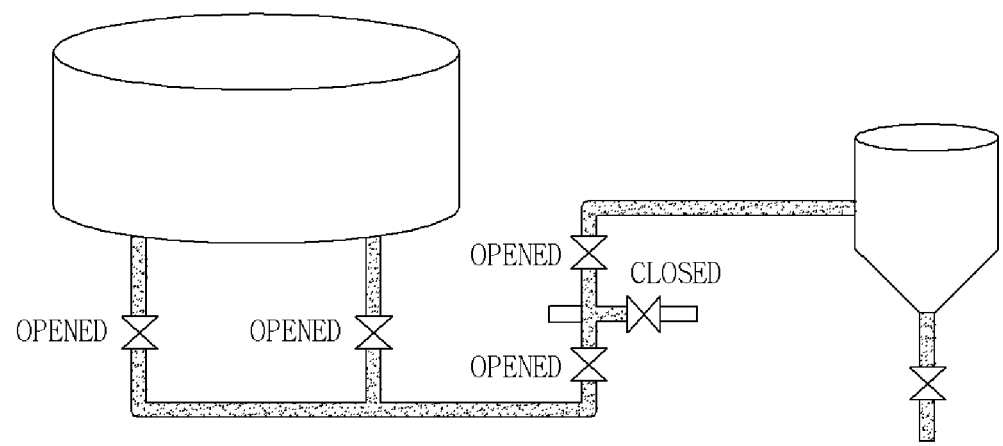

FIG. 3d is a diagram illustrating a cleaning unit replacement stage.

As illustrated in the drawing, the cleaning unit 33 includes a third valve 53 installed in an intersection position of the drain pipe 31. The third valve 53 of the cleaning unit 3 may remain open except for a period during which the brush 332 moves backward. When the third valve 53 is closed, the drain water that flows through the drain pipe 30 is stopped so as not to intrude into the cleaning unit 33. Accordingly, the brush 331 can be easily replaced and repaired while the drain water is continuously drained to the oil-water separator 20.

The present invention has been described with reference to exemplary embodiments illustrated in the drawings, which are provided for only an illustrative purpose. The water drain system for an oil reserve tank according to the present invention is not limited to the exemplary embodiments, but those skilled in the art will apparently appreciate that various alternatives, modifications, and equivalents thereto are possible.

The present invention is intended to cover not only the exemplary embodiments, but also various alternatives, modifications, equivalents and other embodiments that may be included within the spirit and scope of the present invention as defined by the appended claims.

DESCRIPTION OF THE REFERENCE NUMERALS IN THE DRAWINGS

10: Oil reserve tank
20: Oil-water separator
30: Drain pipe
31a: Vertical portion
40: Sump
50: Return pipe

The invention claimed is:

1. A water drain system for an oil reserve tank, comprising:
    an oil reserve tank;
    an oil-water separator separating drain water supplied from the oil reserve tank;
    a drain pipe extending from the oil reserve tank to the oil-water separator, the drain pipe incorporating a horizontal portion and a vertical portion;
    a water detection sensor installed in the vertical portion of the drain pipe in a position that allows contact between the drain water and the water detection sensor while minimizing precipitation of sludge to the water detection sensor; and
    a sensor cleaning unit including a retractable brush, the brush positioned radially in the drain pipe from the water detection sensor, such that the sensor cleaning unit brush faces the water detection sensor, the sensor cleaning unit brush being configured to move radially into contact with the water detection sensor so as to remove sludge from the water detection sensor.

2. The water drain system according to claim 1, wherein the vertical portion enables an upward stream of the drain water.

3. The water drain system according to claim 1, wherein an upstream portion of the drain pipe is provided with a first valve to control drainage of the drain water from the oil reserve tank.

4. The water drain system according to claim 1, wherein the sensor cleaning unit is provided with a valve that controls access to the vertical portion.

5. The water drain system according to claim 1, wherein a return pipe is connected between the oil-water separator and the oil reserve tank.

6. The water drain system according to claim 1, further comprising a sump installed at a downstream side of the oil-water separator.

7. The water drain system according to claim 1, wherein the sensor cleaning unit takes a tubular form and the brush is installed in a tubular portion of the cleaning unit.

* * * * *